(12) United States Patent
Wakeley et al.

(10) Patent No.: US 9,163,279 B2
(45) Date of Patent: Oct. 20, 2015

(54) DEVICE AND APPARATUS

(75) Inventors: Philip Wakeley, Surrey (GB); Graham Gutsell, Berkshire (GB)

(73) Assignee: The Secretary of State for Environment, Food & Rural Affairs, acting through the Animal Health and Veterinary Laboratories Agency, Addlestone, Surrey (GB)

( * ) Notice: Subject to any disclaimer, the term of this patent is extended or adjusted under 35 U.S.C. 154(b) by 0 days.

(21) Appl. No.: 13/505,230

(22) PCT Filed: Nov. 2, 2010

(86) PCT No.: PCT/GB2010/051832
§ 371 (c)(1),
(2), (4) Date: Jul. 5, 2012

(87) PCT Pub. No.: WO2011/051735
PCT Pub. Date: May 5, 2011

(65) Prior Publication Data
US 2012/0270225 A1    Oct. 25, 2012

(30) Foreign Application Priority Data

Nov. 2, 2009 (GB) .................................. 0919159.4

(51) Int. Cl.
*C12Q 1/68* (2006.01)
*B01L 3/00* (2006.01)
*B01L 7/00* (2006.01)

(52) U.S. Cl.
CPC ......... *C12Q 1/6834* (2013.01); *B01L 3/502715* (2013.01); *B01L 3/5023* (2013.01); *B01L 7/52* (2013.01); *B01L 2200/16* (2013.01); *B01L 2300/042* (2013.01); *B01L 2300/046* (2013.01); *B01L 2300/087* (2013.01); *B01L 2400/0406* (2013.01); *B01L 2400/0487* (2013.01)

(58) Field of Classification Search
None
See application file for complete search history.

(56) References Cited

U.S. PATENT DOCUMENTS

| | | | |
|---|---|---|---|
| 2005/0013732 A1* | 1/2005 | Battrell et al. | 422/58 |
| 2006/0275773 A1* | 12/2006 | Wangh et al. | 435/6 |
| 2008/0199851 A1* | 8/2008 | Egan et al. | 435/5 |
| 2009/0226911 A1* | 9/2009 | Mauk et al. | 435/6 |
| 2009/0325276 A1* | 12/2009 | Battrell et al. | 435/287.2 |
| 2010/0035349 A1* | 2/2010 | Bau et al. | 436/43 |
| 2010/0304986 A1* | 12/2010 | Chen et al. | 506/9 |
| 2011/0039261 A1* | 2/2011 | Hillebrand et al. | 435/6 |

FOREIGN PATENT DOCUMENTS

| | | |
|---|---|---|
| GB | 2453356 A | 8/2009 |
| WO | WO99/33559 A1 | 7/1999 |
| WO | WO0166688 A1 | 9/2001 |
| WO | WO 2004065010 A2 * | 8/2004 |
| WO | WO2004065010 A2 | 8/2004 |
| WO | WO2005083423 A2 | 9/2005 |
| WO | WO2006022495 A1 | 3/2006 |
| WO | WO2006041524 A2 | 4/2006 |
| WO | WO2006080021 A2 | 8/2006 |
| WO | WO2007009125 A2 | 1/2007 |
| WO | WO 2007092713 A2 * | 8/2007 |
| WO | WO2007104962 A1 | 9/2007 |
| WO | WO2008103824 A1 | 8/2008 |
| WO | WO2009080817 A2 | 7/2009 |

OTHER PUBLICATIONS

Weigl et al. (Lab-On-A-Card Assay for Enteric Pathogens, PATH, 2006).*
Chen et al. (A Microfluidic System for Saliva-Based Detection of Infectious Diseases, Ann. N.Y. Acad. Sci. 1098: 429-436 (2007)).*
Kim et al. (A Disposable, Self-Contained PCR Chip author manuscript, available online Nov. 18, 2008).*
Wang et al. (A disposable microfluidic cassette for DNA amplification and detection, Lab Chip, 2006, 6, 46-53).*
Zhang et al. (Miniaturized PCR chips for nucleic acid amplification and analysis: latest advances and future trends, Nucleic Acids Research, 2007, vol. 35, No. 13 4223-4237).*
Yager (Microfluidic diagnostic technologies for global public health, NATURE, vol. 442; Jul. 27, 2006).*
Abrams et al. (Development of a Microfluidic Device for Detection of Pathogens in Oral Samples Using Upconverting Phosphor Technology (UPT), Ann. N.Y. Acad. Sci. 1098: 375-388 (2007)).*
Chen et al. (An Integrated, Self-Contained Microfluidic Cassette for Isolation, Amplification, and Detection of Nucleic Acids, Biomed Microdevices. Aug. 2010;12(4):705-19).*
International Search Report and Written Opinion for PCT/GB2010/051832 dated May 7, 2011 (19 pages).
UK Search Report for Application No. GB0919159.4 dated Feb. 25, 2010 (4 pages).

* cited by examiner

*Primary Examiner* — Christopher M Babic
*Assistant Examiner* — Aaron Priest
(74) *Attorney, Agent, or Firm* — Stites & Harbison, PLLC; David W. Nagle, Jr.

(57) ABSTRACT

A device (1) for carrying out a chemical or biochemical reaction and detecting the results is described. The device may be used in an assay to detect a target nucleic acid in a sample. The device includes (i) a well (8) in which a chemical or biochemical reaction such as a nucleic acid amplification reaction may be effected in a liquid phase or a receiver for such a well; (ii) a channel (16) extending from the well; (iii) a lateral flow assay device (32) arranged to receive liquid contents from channel, on a bibulous membrane thereon. The membrane contains elements that are able to detect the products of the chemical or biochemical reaction such as a target nucleic acid. Methods for using such devices and apparatus for carrying out assays using these are also described and claimed.

18 Claims, 8 Drawing Sheets

DEVICE AND APPARATUS

The present invention relates to apparatus and systems for use in carrying out and detecting the products of chemical or biochemical reactions such as the purification and/or detection of nucleic acids in samples such as biological samples, as well as to devices or combinations of devices, in particular disposable units for use in such apparatus and systems, and methods for the purification and/or detection of nucleic acids using said apparatus and units.

The detection of nucleic acids in samples, in particular biological samples, is well known in the fields of research, diagnosis, in particular of disease and genetic conditions, forensics and detection of microorganisms, for example for hygiene, environmental monitoring or military purposes, where potentially harmful microorganisms such as bacteria are required to be detected rapidly.

Lateral flow devices (LFDs) have long been used in the field of diagnostics to detect target analytes such as proteins including hormones, antigens, antibodies etc. In these devices, a liquid sample containing or suspected of containing the analyte flows along a membrane, where it encounters labels, labelled binding partners and/or immobilised binding partners, in a sequence whereby a detectable visible signal is developed on the membrane depending on the presence or absence of the analyte in the sample.

The volume of liquid required to cause a sample to effectively flow along an LFD is generally quite significant. The membrane used as a substrate for the LFD is porous and will generally absorb significant amounts of liquid. Furthermore, the liquid flow must be sufficient to ensure that the labelled moieties are carried through to the detection zone on the device.

They may also be used to detect analytes that comprise nucleic acids such as RNA or DNA. In this case, the binding partners for the analytes will include oligonucleotides that hybridise to the specific target sequence or alternatively, binding partners for binding agents that have been incorporated into the RNA or DNA, for instance during a preliminary amplification reaction. For instance, nucleic acid amplification reactions may also be used to incorporate a binding agent such as biotin, into the target so as to facilitate capture in the detection zone. Where biotin has been incorporated into a target nucleic acid, the presence of strepavidin or anti-biotin antibodies in the detection zone on the LFD will result in capture of biotin-labelled target nucleic acids in the capture zone.

Labelling may be effected using either labelled probes that also hybridise for instance to the target sequence so as to produce a visible signal when the target becomes immobilised in the detection zone, or by incorporating a label into the target sequence, for instance during an amplification reaction, where labelled primers are used to generate an intrinsically labelled product. Suitable labels are well known in the art, chemical or biochemical labels such as fluorescent labels including for instance, fluorescein or fluorescein derivatives, or cyanine dyes, or labels that may be detected enzymatically such as digoxigenin. In another embodiment, labels may comprise particulate labels such as gold, silver, and latex beads or particles, which produce a visible signal directly. These may be arranged to interact with target nucleic acid in the detection zone. In order to achieve this, the particles themselves will be labelled, for example conjugated to, moieties that interact with the target nucleic acid (for example other nucleic acids that hybridise to the target nucleic acid), or they may be conjugated to a binding agent such as streptavidin, that interacts with a binding partner such as biotin, which has been incorporated into the target nucleic acid sequence.

In fact, in most cases, the concentration of target nucleic acid in a biological sample is low, and certainly below that at which a visible signal may be generated directly on an LFD. Thus, as a preliminary step, amplification of the nucleic acid is generally required.

Nucleic acid amplification techniques are a powerful tool in this area. There are many techniques, some of which are carried out isothermally, and some of which require thermal cycling such as the polymerase chain reaction, which allow very small amounts of target nucleic acid in a sample to be amplified to detectable levels.

However, the extreme sensitivity of these techniques means that they are very prone to contamination or cross contamination. Even a very small amount of contaminating nucleic acid may be subject to amplification in these methods, leading to false positives.

Many attempts have been made to address this problem, and they focus principally on ensuring that the sample is treated in an environment isolated from the amplification process as far as possible. Thus methods for carrying out an amplification reaction and detecting the amplification product in a homogenous reaction, where the reaction vessel does not have to be opened, have been developed.

However, it is frequently necessary to subject a biological sample to some pre-treatment steps in order to release nucleic acids for example from eukaryotic and prokaryotic cells or from viruses, so as to allow amplification to proceed. Clearly it is desirable that such procedures are carried out in a manner which minimises any contamination risk.

For example, U.S. Pat. No. 6,649,378, US Patent Publication No. 2004/0110167 and US Patent Publication No. 2006/0160078 describe a range of self-contained devices that integrate nucleic acid extraction, amplification and detection in a single device.

Generally however, such devices require physical manipulations to effect the method. For instance, the devices of U.S. Pat. No. 6,649,378 and US Patent Publication No. 2004/0110167 describe systems in which DNA extraction is carried out in a first device, the contents are transferred to an amplification tube such as a PCR tube, and finally, a lateral flow device ("result stick") is introduced into the tube. Manipulations of this type can result in the introduction of contaminants.

The device of US Patent Publication No. 2006/0160078 describes a system in which extraction, amplification and detection is carried out at various zones on a membrane of an LFD, wherein each of the zones are initially separated, and then brought together sequentially, for example by removal of an intervening plastic sheet or by using a plunger to bring one zone down onto the subsequent zone. In this case however, the volumes of liquid that are present in each stage is to some extent a function of the requirements of the membrane of the LFD and how this absorbs or transmits liquid. However, optimised amplification reactions may preferentially be carried out in solution in small volumes of 'free' liquid which may not be possible under circumstances such as that of US Patent Publication No. 2006/0160078 where the volumes are required to flow though an LFD.

There is a need for an integrated system that allows for analysis to be carried out rapidly without the need for onerous manual operations and with minimal contamination risk and with maximal efficiency.

The applicants have developed apparatus that allows chemical and biochemical reactions such as nucleic acid analysis to be carried out in an isolated unit, which may be disposable, with minimum contamination risk.

In particular, the applicants have designed a device in which a nucleic acid amplification may be carried out in the liquid phase in a well of convenient volume, and the product of that reaction to be transferred to a membrane of a lateral flow device without being exposed to the environment.

As a result, the present invention provides a device for carrying out an assay to detect a target nucleic acid in a sample, said device comprising
(i) a first well in which a nucleic acid amplification reaction of said target nucleic acid may be effected in the liquid phase;
(ii) a first channel extending from said first well,
(iii) a lateral flow assay device arranged to receive sample from said first channel and detect said target nucleic acid therein.

Depending upon the volumes used, liquid passing along the first channel may be delivered directly onto a sample receiving section of a lateral flow assay device. This may comprise a wicking pad. However, in a particular embodiment, where significant volumes are delivered via the first channel, it may be convenient to provide a second well arranged to receive liquid from said first channel. In such cases, the lateral flow assay device is arranged to receive sample from said second well. For instance, a receiving section of the lateral flow assay device may project into the second well. This may be convenient where the volumes being delivered are greater that can be conveniently absorbed directly by a receiving section of the lateral flow device.

Thus in a particular embodiment, the present invention provides a device for carrying out an assay to detect a target nucleic acid in a sample, said device comprising
(i) a first well in which a nucleic acid amplification reaction of said target nucleic acid may be effected in the liquid phase;
(iia) a second well connected to said first well by means of a first channel, wherein the first channel is arranged such that contents of said first well may be transferred to the second well;
(iii) a lateral flow assay device arranged to receive sample from said second well and detect said target nucleic acid therein.

The device of the invention may be a unitary device containing all the elements (i), (ii) and (iii) as well as (iia) where present, in an integral unit or entity. For example, the elements of the device may all be contained within a single housing. However, in a particular embodiment, the device may be modular, in particular so that the first well (i) may be provided as a separate unit that is attachable to the device for use. In such cases, the individual modules, one of which is a device as defined above but with receiving means for the first well instead of a first well and the other of which is a first well adapted for receipt into the receiving means, form further aspects of the invention. Such modular first wells are suitably self-supporting and may be provided with annular flanges or lips so as to facilitate handling and attachment to the receiving means.

As used herein, the term "lateral flow assay device" refers to any assay device that operates by the flow of liquid along a bibulous membrane. Thus this includes conventional "dipsticks" which may be used vertically, as well as devices in which membranes are fixed in a horizontal position so that flow along the membrane occurs horizontally or laterally.

The term "channel" refers to a path defined in a solid body through which liquid can flow freely, for example under the influence of differential pressure and/or gravity, and in particular does not necessarily rely on capillary action.

By combining sections in which liquid is transferred by bibulous flow with sections in which normal liquid flow is permitted within the same device, the device of the invention allows each stage of the assay (amplification and detection) to be carried out under the preferred conditions. Thus the volume of any amplification reaction mixture in the first well may be selected so as to provide optimal amplification conditions. However, that volume may be changed, and in particular increased by addition of diluent, on transfer to the second well, and subsequently to the lateral flow device so as to provide the preferred volumes for use in the lateral flow assay device. Transfer of liquid between the sections of bibulous and normal liquid flow is facilitated by the fact that the sections are contained within the same device. Furthermore, the device is amenable for automatic or semi-automatic operation of the assay.

In a particular embodiment, the second well is closed. The first channel connecting the first well to the second well is suitably enclosed within the device, for example within a housing containing at least the first and second wells.

In another embodiment, the first well is closable.

As used herein, the term "closed" means that the wells are isolated from the atmosphere, although they may be in communication with each other. Similarly, the term "closable" refers to a well that may be isolated from the atmosphere, for example by means of a lid, cap, plug or seal. In the case of modular devices, where the first well is provided as a separate but attachable element of the device, the device itself may provide the lid, cap, plug or seal of the device. In such instances, the device is provided with a suitable receiving means such as a downwardly projecting protrusion or spigot, that fits into the opening of the first well, for example by means of a snap or screw fit. In such cases, provision must be made in the attachable first well to accommodate the first and where present, second channel as described below so that they are not blocked by the walls of the first well when it is in position in the device. For instance, the first and where present second channels suitably pass through the protrusion or spigot so as to open into a first well when it is in position on the receiving means, but other arrangements may be envisaged.

Where the second well is closed and the first channel is also enclosed, amplification reactions can be conducted and the resultant amplification product transferred to a lateral flow device for detection without exposure to the atmosphere, therefore minimising risk of contamination.

In a particular embodiment, the device further comprises
(iv) a third well suitable for containing diluent and connected to said first well, by means of a second channel, wherein the second channel is arranged such that diluent from said third well may be transferred to the first well. This embodiment means that the amplification reaction can be carried out in a small volume of liquid, which is preferable or even optimal for the amplification reaction, and the amplification product may be diluted sufficiently prior to entry into the second well to allow it to flow freely along the lateral flow device, by addition of the diluent. The third well may contain preloaded diluents and be closed as defined above. However, since the well may be open to the first and second channels and thus to the membrane of the lateral flow device which may be hydroscopic, the applicants have found that it may be advantageous to add the diluent at the last possible moment. In order to allow this to be part of an integrated kit, in a particular embodiment, the diluents is supplied inside a sealed container, openable within the third well only when diluents are required for use. Thus for instance, diluent may be contained within a sealed flexible pouch, blister pack or ampoule which is accommodated within the third well or supplied in contact with it, and means for opening the pouch or ampoule such as piercing means like a pin or cutter provided within the third well. The piercing means is arranged so that the diluent container is only punctured or opened when pressure is applied to the container or the piercing means during the process. For instance, the piercing means may be provided within the base of the third well, and the diluents container may be forced into piercing contact with it at the required time. This prevents liquid diluent from prematurely contacting the membrane of the lateral flow device before it is used, which may cause the device to deteriorate.

The first well is adapted to allow specifically a nucleic acid amplification reaction to be carried out therein. Such reactions are generally carried out in relative small volumes and thus the volume of the first well will be relatively small as discussed further below.

In particular however, the first well is suitably adapted to make it available for heating to the desired temperatures generally undertaken in a nucleic acid amplification. Thus the well is suitably constructed of a material which is resistant to such temperatures and/or temperatures fluctuations and changes that are involved in a typical nucleic acid amplification reaction.

In particular embodiments, the first well is arranged on a projection or limb of the device so that it is readily available for heating and/or cooling to effect a nucleic acid amplification, for example using external heating devices or, where appropriate, thermal cyclers.

In a particular embodiment, the first well is of smaller volume to the second well where present and third wells. For example, the first well may have a capacity of from 10-250 µl such as from 15-50 µl, for example about 25 µl, whereas the second and third wells suitably have capacities in the range of from 40-4000 µl, for instance from 40-2500 µl. In a particular embodiment, the second and third wells may have capacities of about 2500 µl. In other embodiments, the capacities of the wells may be from 40-1000 µl such as from 50-250 µl, for example about 100 µl. For instance, the diameter of the first well may be in the range of 2-3 mm with a depth of about 4-10 mm for example about 5 mm, whereas the diameter of the second and third wells may be in the range of 7-20 mm for example about 10 mm with a similar depth.

This arrangement means that the device is suitable for carrying out a range of chemical or biochemical reactions where the reaction itself is optimally effected in a relatively small volume of liquid, and that volume is generally smaller than that required to effectively provide a signal on a conventional lateral flow device. Thus in a further aspect the invention provides a device for carrying out a chemical or biochemical reaction and detecting the product thereof, said device comprising (i) a first well in which a chemical or biochemical reaction may be effected in a liquid phase;
(ii) a first channel extending from said first well,
(iii) a lateral flow assay device arranged to receive liquid contents from said first channel, optionally by way of a second well, on a bibulous membrane thereon, wherein said membrane contains elements that are able to detect product of said chemical or biochemical reaction, and
(iv) a third well that is arranged to contain diluent and connected to said first well, by means of a second channel, wherein the second channel is arranged such that diluent from said third well may be transferred to the first well, and wherein the capacity of the second and third wells is significantly greater than that of the first well.

Preferred embodiments of such devices will operate in a similar manner to embodiments described herein, but the membrane of the lateral flow device will be loaded with appropriate detection reagents. Such chemical and biochemical reactions may comprise any form of chemical or biochemical reaction.

Suitably the lateral flow assay device is fully enclosed within the device, for example it is encased within a housing of the device, also to minimise the risk of contamination. In this case, a viewing window is suitably provided in the device or housing to allow the results of the assay to be read, or any housing itself is of a transparent material.

The lateral flow assay device may be arranged so that the membrane projects into the second well and thus absorbs sample directly from the second well. In a particular embodiment however, a liquid flow element, in particular a wicking element is arranged to receive sample from the second well and transfer it to a sample receiving section of the membrane of the lateral flow device. Suitable wicking elements include a pad of wicking fibre, for example constructed from a dense, hydrophilic fibrous material such as cellulose or the like. The wicking element at least projects into the second well at one end, and makes contact with an end region of the membrane of the lateral flow assay device at the other, to ensure that liquid transfers from the second well onto the membrane in an acceptable and controlled flow. In a particular embodiment, the wicking element lines the base of the second well so that liquid delivered into the well is applied directly to the wicking element.

The wicking element may itself act as a reservoir for reagents used in the lateral flow assay device to develop a signal. For instance, binding partners for the amplified target nucleic acid which are suitably labelled as described above, may be stored within the wicking element. These are then transferred with the sample along the membrane of the lateral flow assay device to the appropriate detection zone on the membrane.

The device is suitably a disposable unit intended for single use. At least a part of the device and preferably the entire device is suitably contained within a housing which is suitably of a rigid plastics material.

The first well can be heated or cooled in a controllable manner. Although heating elements such as resistive heating elements, or cooling elements or thermostat elements as well as temperature control or temperature measurement elements such as thermistors or thermocouples may be included within the device itself, in a particular embodiment, the first well is arranged to be adjacent to, in contact with or otherwise encompassed by such elements within an apparatus, adapted to accommodate the device for assay purposes. The device is suitably adapted to fit into the apparatus so that the first well may be subject to heating which is suitably controlled heating.

Thus for example, the first well may extend outwardly of the housing for instance on a projection as described above, so that it may be accommodated within a corresponding well within a heating or thermocycling element such as a block heater which optionally forms part of the apparatus. Alternatively, the projecting well may be arranged to fit within an air cooling or heating chamber of for example a forced air heater, thermal cycler or a thermostat.

Alternatively, the device may include grooves, channels or other indentations, arranged so that heating or thermostat elements within the apparatus project into the device around or in the vicinity of the first well when the device is positioned within the apparatus, so as to allow the controlled heating of the contents of the first well.

Material is suitably transferable through the first and/or second channels under pneumatic, hydraulic or vacuum controlled flow. For example, in some embodiments the housing further comprises a first port, linked to the said third well. The port is suitably normally sealed, but just before or on introduction of the device into an apparatus for carrying out the assay, it is opened and becomes connected to a kinetic energy source for example a source of hydraulic or pneumatic pressure or vacuum, that is able to drive the diluent from the third well into the first well. A vent port, connected to the second well may be provided so as to allow liquid flow through the channel between the well.

The energy source is suitably a pump which is connected to the third well and arranged to operate automatically when required after completion of the amplification reaction, but it may also comprise a simple plunger device that may be operated manually to drive the diluent from the third well into the first well and thereafter into the second well hydraulically. In the latter case, it may be preferable to first draw the plunger up slightly so as to draw the contents of the first well back into the third well as a preliminary mixing operation, before depressing the plunger to drive the thus formed mixture back through the first well and into the second well.

Alternatively, the diluent may be drawn from the third well into the first well by application of reduced pressure or a vacuum, applicable within the apparatus. This will be effected using a similar, normally sealed port within the device, linked to either the first or second wells. Within the apparatus, the said sealed port will become connected to a source of vacuum so as to generate the required liquid flow within the device.

If desired, more efficient mixing of the contents of the first well with the diluent may be achieved by providing one or more additional diluent containing wells within the device. These are suitably arranged so that separate streams of diluent are fed into the second well together with the contents of the first well. Suitably the streams will converge before entering the second well so as to induce turbulent flow which provides enhanced mixing of the contents from the first well with the diluent, before it is applied to the lateral flow device.

The flow from multiple diluent wells is suitably coordinated and controlled to ensure beneficial mixing. This can be arranged using a control system for the hydraulic, pneumatic or vacuum pressure. Where the diluent is applied using a series of plungers, these may suitably be interconnected for example using a lever or cantilever device, arranged to ensure that the flow from individual wells is coordinated automatically, when pressure is applied to the lever.

The channels themselves will be arranged to facilitate the necessary transfer. Thus for example, the first channel may connect to the base of the first well so that all the material can be removed from it when the driving pneumatic pressure or vacuum is applied. The first channel may enter the second well in an upper region thereof. Similarly the second channel may link to the base of the third well and connect to an upper region of the first well.

When the second well is of greater capacity than the first well, diluent drawn or delivered into the first well will effectively overflow the first well, into the second well. However, the application of pneumatic pressure to the diluent in the third well may be continued until the contents have passed through the first well and been delivered to the second well. Alternatively, a similar normally sealed vacuum port may be provided in the device, linked to the second well to draw liquid from the third well by way of the first well into the second well. Thus the product of any amplification in the first well may be delivered in dilute form to the second well.

In general, an end region comprising the sample receiving zone of the membrane of the LFD will be located within the second well so that liquid containing any amplified nucleic acid is absorbed into the membrane and will wick along the length thereof. One or more detection or control zones, in which suitable binding partners for target moieties are immobilised, are provided on the membrane downstream of the said one end in the conventional manner, so that target nucleic acids are captured (or otherwise in the case of a competitive assay format) in said zone. The nucleic acids are suitably labelled either directly during the amplification reaction or by contact with a labelled probe, which is either introduced into the amplification reaction or movably located on the LFD. Thus accumulation of labelled material for example, associated with particulate labels (e.g. latex beads) as described above in a detection zone gives rise to a visible signal in the LFD. Examples of such devices are illustrated for example in US2004/0110167.

Suitable membranes may comprise cellulose based materials such as cellulose, nitrocellulose, or carboxymethylcellulose, hydrophilic polymers including synthetic hydrophilic polymers such as polyesters, polyamides, carbohydrate polymers, hydrophobic polymers such as halogenated polymers such as polytetrafluoroethylene, fibreglass or porous ceramics.

Particularly suitable membranes include cellulose membranes and in particular nitrocellulose membranes which may be laminated, such as those available from Millipore. These may be supported on a backing material such as a plastic backed membrane such as a polyester (Mylar®) or PET backed cellulose membrane.

The backing of such membranes are naturally hydrophobic whereas the cellulose itself is hydrophilic, which gives rise to the necessary wicking effect. However, the hydrophilicity can give rise to problems when these are used in the context of an immunoassay procedure. The membranes used in these devices may if required, be blocked using conventional blocking agents. Blocking agents are those that may reduce non-specific interactions between any protein in the sample and the membrane or increase the wicking rate of the sample. They are generally applied after the application of immobilised binding agents and are usually selected from three types of agent including proteins, surfactants and synthetic polymers. Particular examples of proteins which may be used as blocking agents include bovine serum albumin (BSA), of non-fat dry milk components such as casein.

Examples of surfactants which may be used as blocking agents include non-ionic surfactants such as polyoxyethylene sorbitan monolaureate which is sold under the trade name of Tween™ 20 and octylphenol ethoxylates for example as sold by Dow as the Triton X™ series, for example Triton X-100.

Suitable synthetic polymers for use as blocking reagents include polyvinyl alcohol (PVA), polyvinylpyrroline (PVP), polyethylene glycol (PEG) and polyoxyethylene fatty ethers such as those derived from lauryl, cetyl, stearyl and oleyl alcohols and sold under the trade name Brij™.

It is generally recognised that mixtures of two or more of these types or classes of blocking reagent may be particularly employed, for example a mixture comprising a surfactant and a synthetic polymer as outlined above.

In a preferred embodiment however, no blocking agent is used on the membrane.

Reagents for carrying out the amplification, such as primers, enzymes, probes etc. may be preloaded into the first well so that it is ready to receive sample directly for amplification. In particular such reagents may be present in dried and in particular freeze dried form, to ensure that they do not decompose or react prematurely. However, in a particular embodiment, such reagents are introduced into the device by use of a reagent dispenser which is suitably in the form of a "plug", wand or cap, having the reagents freeze dried on an outer surface thereof. The reagent dispenser therefore also acts to close the first well once the reagents have been added.

Such reagent dispensers may be supplied separately to the devices since these will be specific to a particular nucleic acid assay, whereas the devices themselves may be used generally in a range of assays. However, they may be supplied in combination with the devices, and thus the invention further provides a combination of a device as described above and a reagent dispenser (or a plug, wand or cap). The reagent dispensers such as the plugs, wands or caps are suitably supplied in a sealed container, which is packaged separately from other elements of the combination such as the device, so as to ensure that they remain free of moisture.

In either case, it is preferred that liquid components of the amplification reaction such as the amplification buffer is introduced into the first well only at the start of the amplification reaction. This minimises contamination risks and also prevents premature reactions occurring.

In order to achieve this, the device suitably comprises a closed fourth well, preloaded with liquid reagents such as assay buffers. Thus this fourth well acts as a reservoir for the reagents. It is also linked to the first well by means of a channel so that the contents may be delivered into the first well when required to carry out an amplification reaction. Again elements of a pneumatic, hydraulic or vacuum system such as a channel to a pneumatic or vacuum port is also provided so as to allow the contents of the fourth well to be driven or drawn into the first well at the appropriate time. These elements are arranged to operatively interact with the corresponding pneumatic or vacuum elements in the apparatus designed to accommodate the device for carrying out the assay.

Similarly, the apparatus will comprise heating means adapted to interact with the first well as described above in a manner which allows the desired amplification reaction to be carried out in the well. Generally, it is preferable that the amplification reaction conducted is one of the many isothermal amplification reactions known in the art such as nucleic acid sequence based amplification (NASBA), strand displacement amplification (SDA), transcription mediated amplification (TMA), Loop-Mediated Isothermal Amplification (LAMP), Q-beta replicase and rolling circle amplification, 3SR, ramification amplification (as described by Zhang et al., Molecular Diagnosis (2001) 6 No 2, p 141-150), recombinase polymerase amplification (available from TwistDx) and others. This requires less complex heating arrangements than thermal cycling reactions such as polymerase chain reaction. However, it would be possible, if the apparatus included thermal cycling means, to carry out amplification reactions such as the polymerase chain reaction or ligase chain reaction, that require thermal cycling.

The sample may if required and if a sample is available in a suitable form, be added directly to the first well. However, in general, as mentioned above, it is necessary to extract and purify nucleic acids from samples, in particular biological samples.

In accordance with a preferred aspect of the invention, the device further includes a nucleic acid extraction and/or purification system. Whilst this may take various forms, a particularly preferred means of extracting purified nucleic acids from a sample involves the use of a bibulous membrane, as described in WO2007/104962, the content of which is incorporated herein by reference. By allowing a liquid sample to flow along a bibulous membrane of the type described above in relation to LFDs, it has been found that nucleic acids become bound to the surface of the membrane which therefore provides a means for separating the nucleic acid from the remainder of the material in the sample. Thus in a particular embodiment, a bibulous membrane for nucleic acid extraction and purification purposes is incorporated into the device.

The membrane is suitably substantially fully encased within the device to minimise risk of contamination. It is arranged to extend between a fifth well, which acts as a sample holding or receiving well and the first well, so that sample in the fifth well can wick along the membrane to the first well. Suitably, the membrane extends at least partially over the opening of the first well. With this arrangement, a small section of the membrane can be cut from it, for example using a cutter provided on the plug, wand or cap described above. This action causes the section of membrane to drop into the first well, whereupon it may be mixed with other reagents on the plug, wand or cap, and the buffer from the fourth well to form an amplification reaction mixture. Any nucleic acid present on the section of membrane can then be amplified.

Although in some cases, the fifth well may act as the sample receiving well, it is generally preferable that a sample is subject to some prior processing, for example to lyse any cells or micro-organisms present in the sample to release cellular contents before nucleic acid is extracted from it. For this purpose, the fifth well may be closed as described above, but connected to an open sixth well provided in the device, by means of an appropriate channel. In this case liquid sample may be added to the sixth well for a preliminary lysis step, before being transferred to the fifth well and the end region of the bibulous membrane. Transfer in this case will suitably be effected using a kinetic energy source such as hydraulic or pneumatic pressure source or a vacuum source as described in relation to the other liquid transfer operations described above, and thus the fifth and sixth wells will be provided with suitably arranged ports for connection to the kinetic energy system of the apparatus. In the case of there being a pneumatic system, suitable vent ports linked to the fifth well may also be required.

Cell lysis may be effected in a variety of ways. For example, a chaotropic agent such as guanidine hydrochloride or a detergent may be added to the sample receiving well, or it may be pre-dispensed therein. However, suitable methods by which cell lysis is achieved in the sample receiving well can be by essentially physical means such as the application of heat or sonication, and in particular by heating the well to temperatures of about 100° C. in the sample receiving well. The apparatus into which the device is positioned for the assay is thus provided with heating means able to effect this process, or a sonication device.

The sample receiving well (whether it is the fifth or sixth well) is suitably closable, for example by means of a cap or plug once the sample has been added to it, and before or after the device has been positioned within the apparatus for the purposes of effecting an assay.

Where liquid samples are obtained, these may be added to the sample receiving well (whether it is the fifth or sixth well) prior to the operation of the lysis operation. However, if the sample is in a solid form such as swab sample, then the swab may need to be washed to release the test material. In this case, the device may be provided with a seventh well which is suitably closed and which contains a wash fluid. The seventh well is connected to the sample receiving well and provided with suitable connections to the pneumatic, hydraulic or vacuum system of the apparatus to allow the contents of the seventh well to be transferred to the sample receiving well for washing of the solid sample at the appropriate time.

Thus in use, the device described above is loaded into apparatus adapted to receive it. Once in position in the apparatus, the various pneumatic or vacuum ports provided in the device become connected to the pneumatic, hydraulic or vacuum system of the apparatus. In addition, controllable heating elements provided in the apparatus are able to interact with the first well for the purposes of carrying out a nucleic acid amplification reaction therein, and optionally also with a sample receiving well so as to instigate cell lysis by heat if necessary. The apparatus is suitably programmed to effect various stages of the process, including transferring liquids from one well to another and heating the appropriate wells automatically, in a sequence that ensures that nucleic acid is extracted from a sample, purified, amplified and detected in a single operation.

Such apparatus forms a further aspect of the invention, as does a system comprising a device and apparatus as described above, including optionally also the reagent dispenser.

Thus in a particular aspect, the invention further provides apparatus for carrying out a chemical or biochemical reaction and detecting the product, in particular in an assay to detect a nucleic acid in a sample, said apparatus comprising:
i) means for receiving a device as described above, and
ii) heating means arranged to controllably heat said first well so as to allow a nucleic acid amplification reaction to be carried out therein.

Where required, the apparatus may further comprise a (iii) a transport system, in particular a pneumatic, hydraulic or vacuum system, connectable to said device so as to allow transfer of material between wells in said device. However, where the device comprises one or more plungers for effecting transfer of liquid diluent as described above, the transport system may be an actuator for said plunger or a lever as described above, or the plunger or plungers may be operated manually.

The apparatus suitably further comprises a control system, such as computer control system, that will effect the desired assay procedure automatically within the device, by controlling the transport system.

If appropriate and where the device comprises a well in which cell lysis is intended to take place (i.e. the sixth well as described above), the apparatus further includes means for heating said well to effect lysis.

The applicants believe that they are the first to combine pneumatic, hydraulic or vacuum controlled liquid flow together with bibulous or capillary flow to effect and analyse a complex biochemical reaction as described above.

In a further aspect the invention provides a system for carrying out an assay to detect a nucleic acid in a sample, said system comprising a device comprising an amplification reaction chamber, a first bibulous membrane arranged to extract nucleic acid from a sample and deliver it to the amplification chamber and a second bibulous membrane arranged as a lateral flow device to detect nucleic acid within an amplification product obtained in said chamber; and means for delivering the product obtained in the amplification chamber to a sample receiving zone of said lateral flow device.

The device, apparatus and combinations of the invention give rise to a useful and easy to operate means of carrying out nucleic acid amplification and detection. By storing reagents necessary in the process in closed wells in the device and making the device disposable, contamination risks are minimised.

In a further aspect, the invention provides a method for carrying out an assay to detect a nucleic acid in a sample, said method comprising adding a sample to a device according to any one of claims 1 to 13, adding a reagent dispenser according to claim 14 or claim 15 to said device, loading said device into apparatus according to any one of claims 17 to 19 and causing said apparatus to carry out a nucleic acid amplification and detection reaction therein, reading the results from the LFD.

The invention will now be particularly described by way of example with reference to the accompanying diagrammatic drawings in which.

Figure 3:
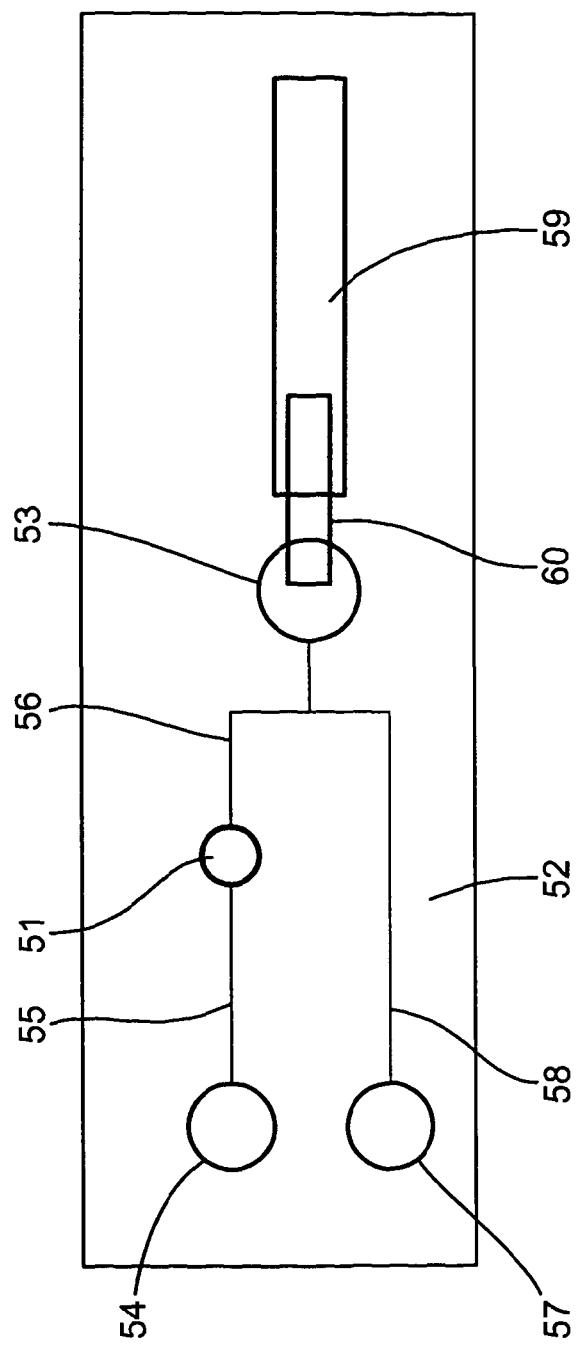
Figure 4:
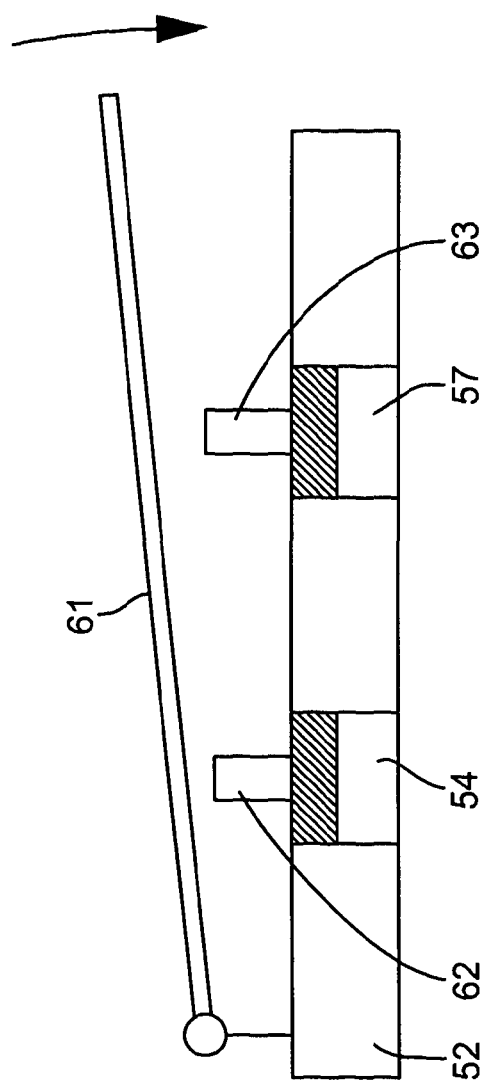
Figure 5:
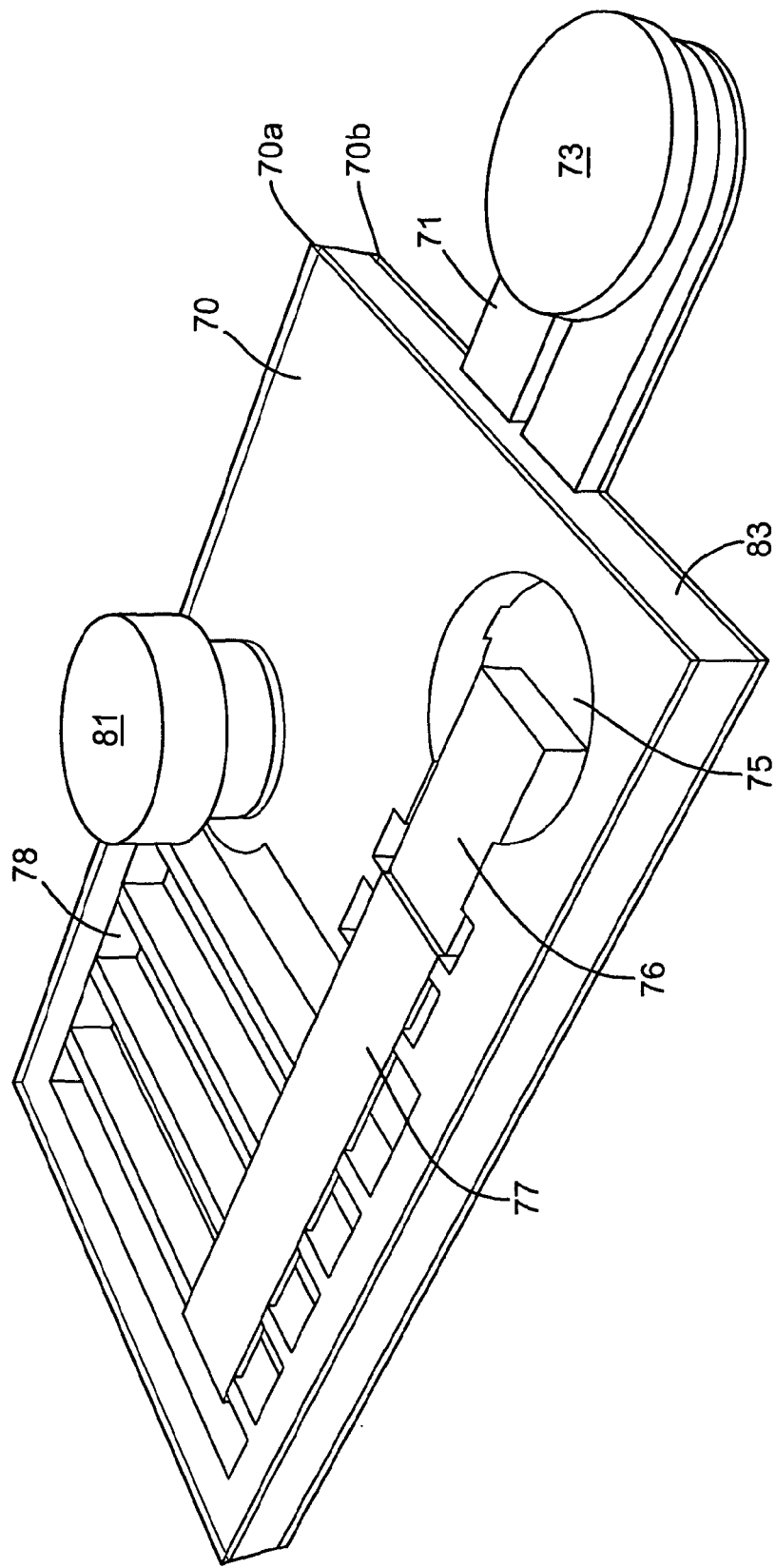
Figure 6:
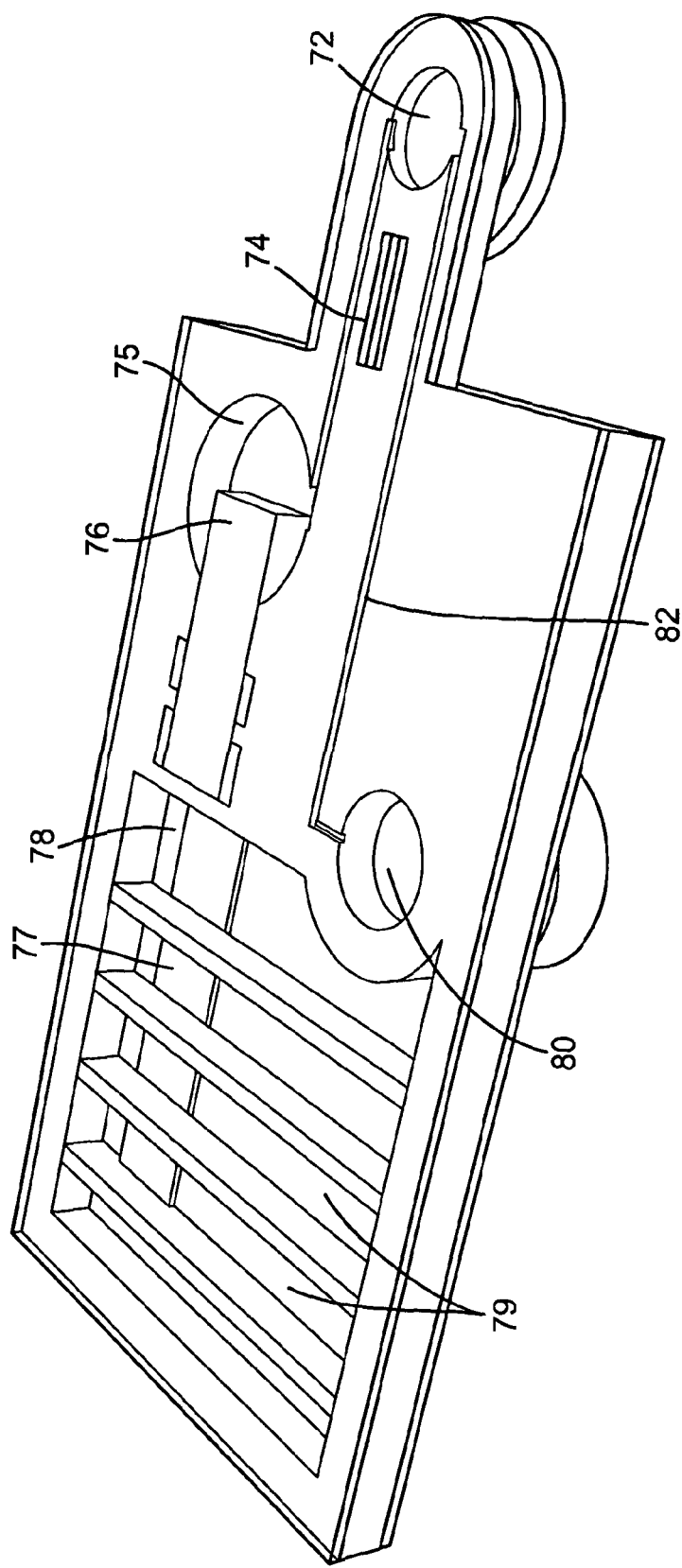
Figure 7:
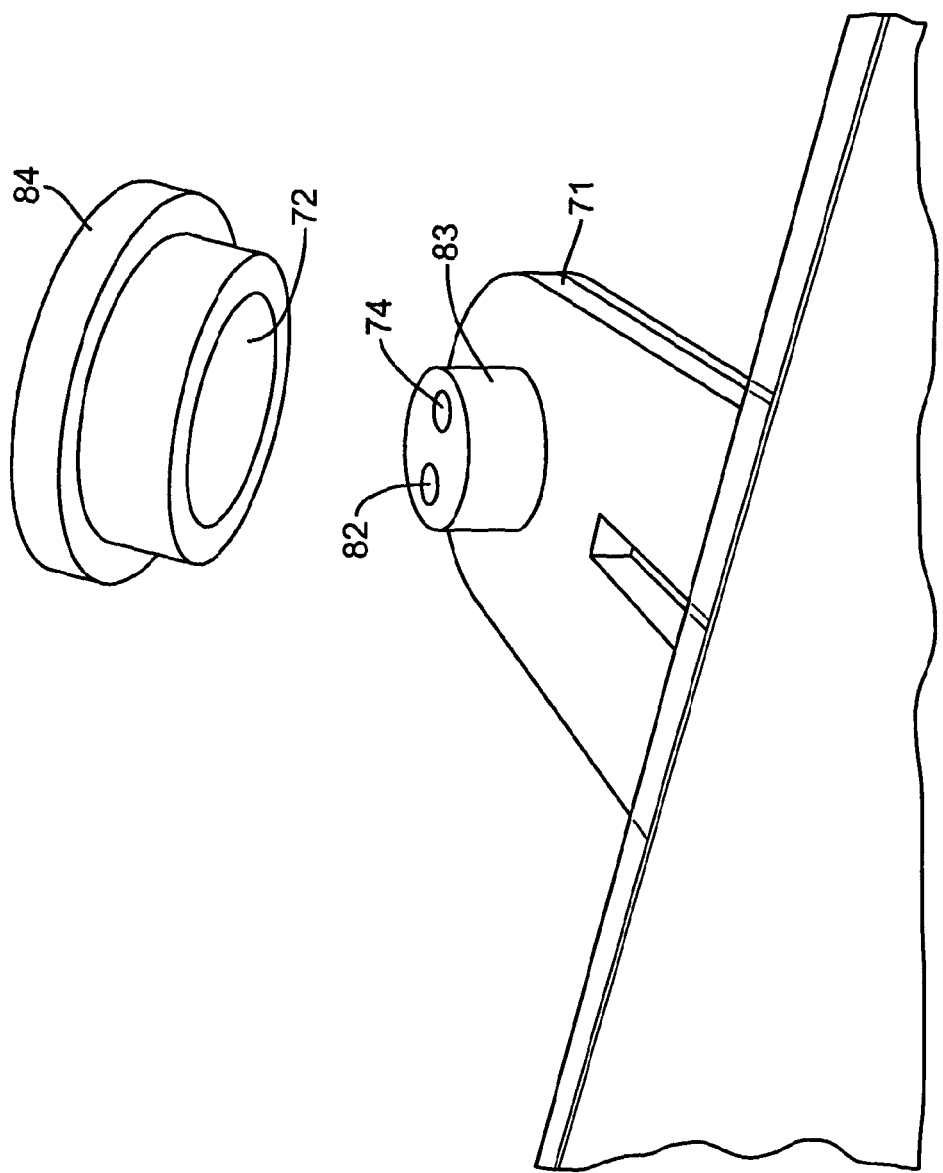
Figure 8:
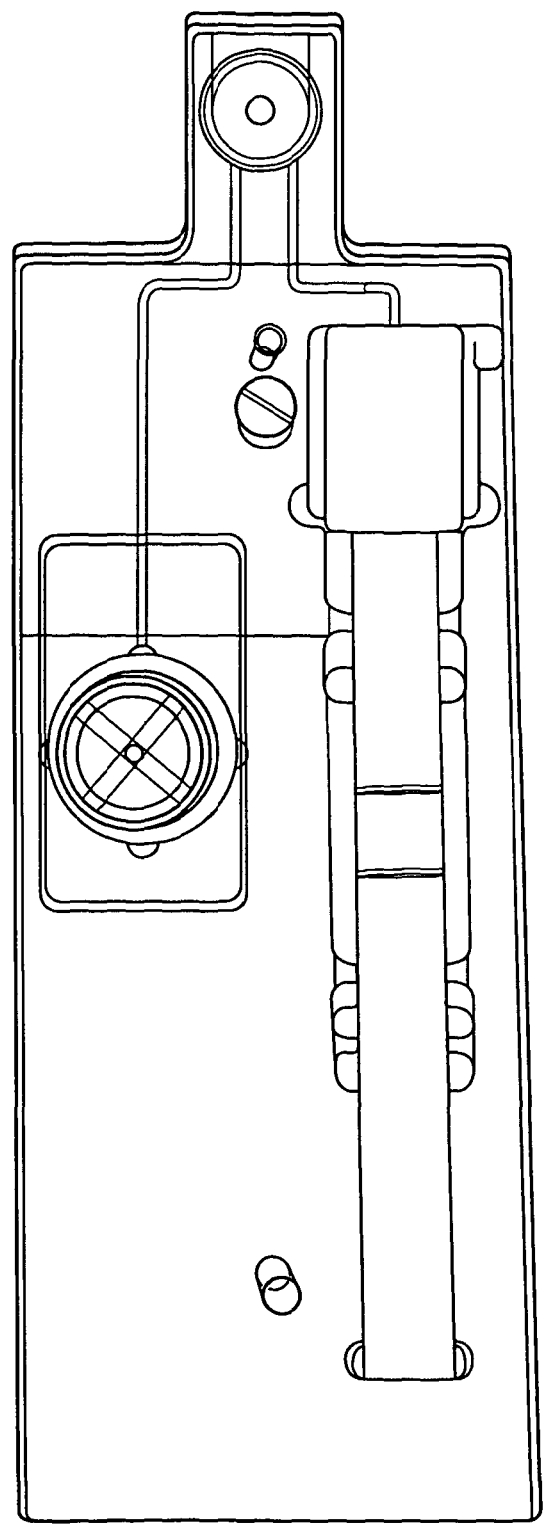

FIG. 3 is a schematic plan view of an alternative form or a device according to the invention, FIG. 4 is a schematic side view of the device of FIG. 3, FIG. 5 is a schematic plan view of another alternative form of a device according to the invention, FIG. 6 is a schematic underside view of the device of FIG. 5, FIG. 7 is a schematic underside view of a part of a device of the invention but with an alternative arrangement of the first well to that shown in FIG. 5, and FIG. 8 is an illustration of a device of the invention after use in a model assay.

EXAMPLE 1

Figure 1:
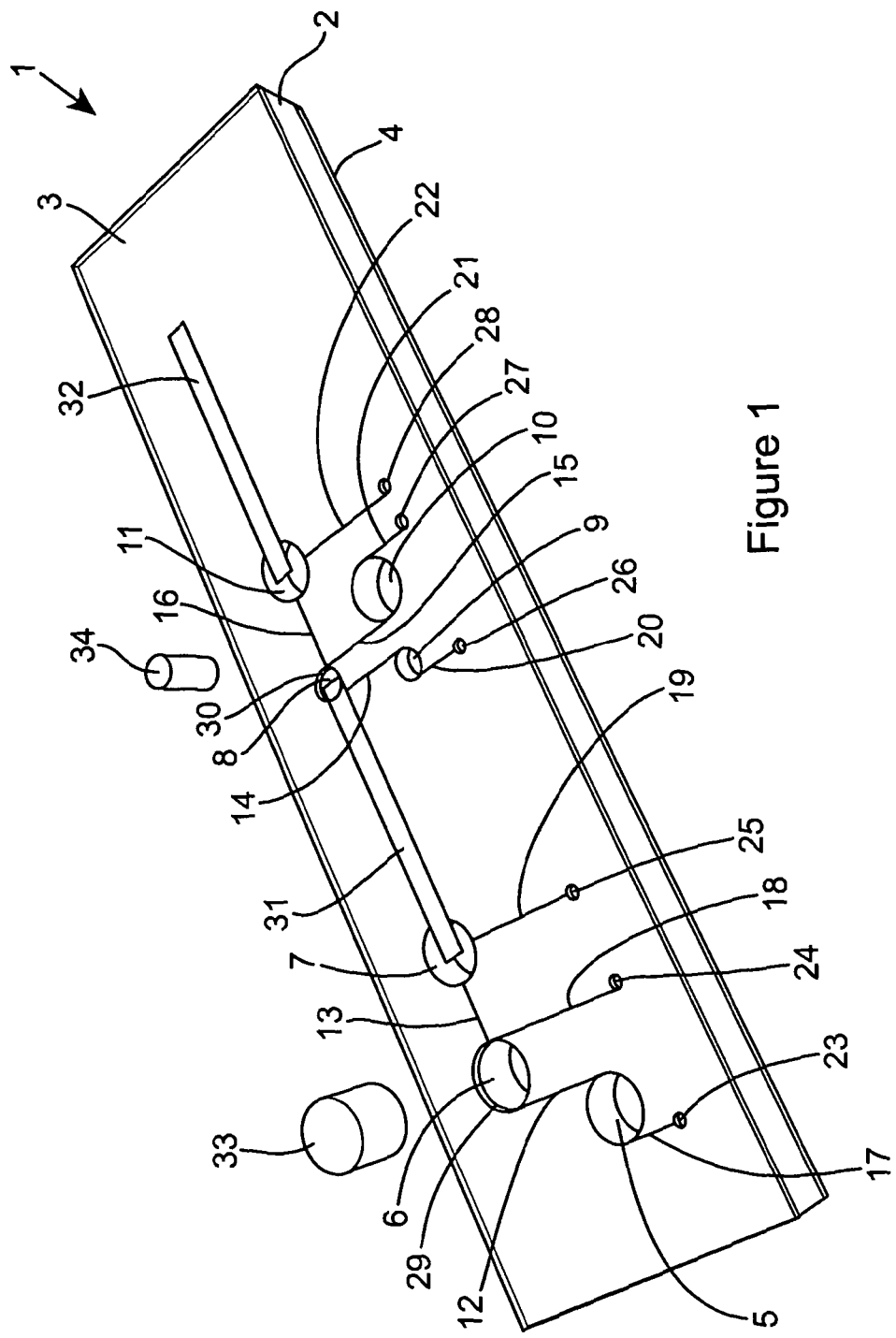
FIG. 1 is a schematic illustration of a disposable device according to the invention, arranged for extraction of nucleic acid from a sample as well as amplification of the extracted nucleic acid and detection of the amplification product.

The device of FIG. 1 comprises a plastics housing (1) which is essentially of a laminar construction comprising a central block (2) sandwiched between an upper cover plate (3) and a lower base plate (4). The central block (2) includes a number of wells (5, 6, 7, 8, 9, 10 and 11) therein together with channels (12, 13, 14, 15, and 16) linking the wells as shown. Additional channels (17, 18, 19, 20, 21 and 22) link most of the wells to pneumatic ports (23, 24, 25, 26, 27 and 28 respectively) provided in the upper cover (3) of the housing (1). The cover (3) further includes an opening (29) aligned with one of the wells (6) to allow it to act as a sample receiving well, and a further opening (30) aligned with another of the wells (8) which acts as an amplification chamber. However, all remaining wells are effectively sealed by the cover (3).

A bibulous membrane (31) is arranged within a horizontal passage in the body (2) and extends between well (7) and well (8), the amplification chamber. The opposed ends of the membrane (31) are located in each of the wells (7) and (8) so that liquid within well (7) will wick along the membrane towards well (8). Suitably, at least a portion of the membrane (31) extends across the opening (30) in the cover (3).

A similar passage within body (2) extends away from well (16) and in this passage is accommodated a lateral flow device (32).

A plug (33) is provided to close well (6) after a sample has been received into it. Another plug (34) is provided to close the amplification chamber well (8). Suitably however, the plug (34) carries at least some of the reagents necessary for effecting an amplification reaction on freeze-dried form on the surface. It may also comprise a cutter (not shown) adapted to cut a sample from the membrane (31) extending across the opening (30) of the well (8) as the plug (34) is pushed into the well. The cut sample then drops into the well (8) ready for amplification.

Certain reagents used in the extraction/amplification/detection process are pre-loaded into some of the closed wells. In particular, a sample wash liquid is loaded into well (5) which acts as a sample wash reservoir. Similarly, buffer for use in the amplification reaction is loaded into well (9), which is suitably of similar dimensions to that of the first well (8). Finally, an elution diluent is loaded into well (10).

Before use, a disposable cover such as an adhesive plastic tape, film or sheet is applied over the cover (3) so that the openings (30, 31) and ports (23, 24, 25, 26, 27 and 28) are sealed for two purposes; first, to prevent atmospheric contamination (thus the wells within the device and where appropriate their contents remain pure) and second, to prevent any airflow through the ports and thereby retaining the liquids in their respective wells.

In use, the following sequence of operation is applied:

- the user unpacks the device (1), removes the tape from the cover (3) to expose the pneumatic ports (23, 24, 25, 26, 27 and 28) and the sample and amplification wells (30, 31). The device (1) may then be loaded into an apparatus adapted to accommodate the device such that the pneumatic ports (23, 24, 25, 26, 27 and 28) become connected to a pneumatic supply. In addition, the wells (6, 8) are aligned with suitable heating or thermostat devices in the apparatus.
- if a liquid sample is to be used, the user loads it onto the well (6) acting as a sample port and the sample plug is inserted.
- if the sample is derived from a swab, the apparatus drives (via pneumatic port 23 and channel 17) sample wash reagent from the sample wash reservoir well (5) along channel (12) into the sample well (6) and the user inserts the swab to wash off its contents. The sample plug (33) is then inserted into the sample well (6).
- the sample well (6) is heated by the apparatus (to approx 100° C.) to extract DNA from the sample matrix.
- the apparatus then drives (via pneumatic port 23 or 24 and channels 17 and 12 or 18 respectively) the extraction product into the adjacent well (7) via channel (13) to make contact with the membrane 31 (venting via channel 19 and pneumatic port 25).
- the apparatus then remains dormant for a sufficient period of time to allow the sample to transit by capillary action along membrane (31).
- the plug (34) carrying reagents such as amplification specific primers, enzymes etc. needed to carry out an amplification reaction dried onto an outer surface thereof is then inserted into the well (8) acting as amplification chamber. The plug (34) carries a cutter arranged so that as it is inserted into the well (8) (either manually by the user, or automatically by the apparatus) it punches out the tip of membrane (31) which drops into the bottom of the well (8).
- the apparatus drives (via pneumatic port 26 and channels 14 and 20) the liquid assay reagents such as buffer and salt solutions into the well (8) (venting via channels 16 and 22 to pneumatic port 28).
- the well (8) is then subject to heating conditions suitable for carrying out a nucleic acid amplification reaction. For example, the well (8) is heated by the instrument to a temperature suitable for performing isothermal amplification, which, in most cases, will be in the range of from 15-85° C., more particularly between 20-80° C. for example at approximately 65° C.
- on completion of the amplification reaction, the apparatus drives diluent (via pneumatic port 27 and channels 21 and 15) from well (10), so that it passes through well (8) collecting the amplification products and transferring the mixture into the adjacent well (11) (venting via channels 16 and 22 to pneumatic port 28) to make contact with a sample receiving zone of the lateral flow device (32). The lateral flow device (32) is set up to produce one or more detectable signals such as a visible target and control lines, in response to the presence or absence of the target nucleic acid or acids in the sample.
- the instrument allows time before requesting the user to read the result from lateral flow device (32) and remove the device (1) from the apparatus.

The process is suitably automated, so pressure is applied to the relevant pneumatic ports in an appropriate sequence. When not used, valves within the apparatus may effectively close the ports (23, 24, 25, 26, 27 and 28).

EXAMPLE 2

Figure 2:
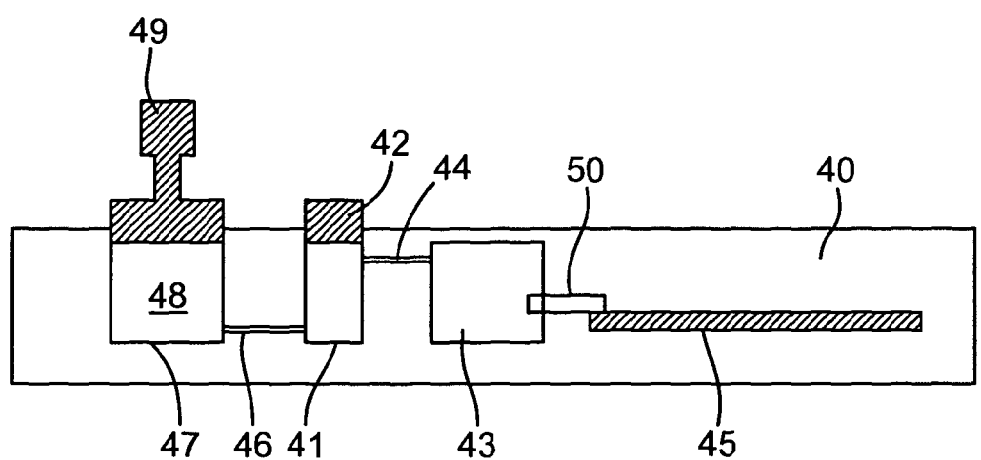
FIG. 2 is a schematic illustration of an alternative form of disposable device according to the invention, for the amplification and detection of nucleic acid in a sample.

An alternative device in accordance with the invention is shown in FIG. 2. In this case, a housing (40) comprises a first well (41), which is closable by means of a cap (42). The first well (41) is linked to a second well (43) by way of a channel (44). The channel (44) is linked to the well (43) in an upper region thereof. Both the channel (44) and the second well (43) are embedded within the housing (40).

A lateral flow device (45) comprising a bibulous membrane provided with reagents necessary to detect a target nucleic acid, projects into the well (43) in a lower region thereof.

A further channel (46) extends between a lower region of the first well (41) and a diluent reservoir (47), also located within the housing (40). The diluent reservoir (47) is filled with diluent (48) and is sealed from the environment by means of a plunger (49).

In use, a sample containing or suspected of containing a target nucleic acid and reagents necessary for carrying out an amplification reaction are loaded into the first well (41). The well is then closed with the cap (42) and the device exposed to conditions, for example temperature conditions, whereby any target nucleic acid sequence present in the well (41) is amplified and any binding agents or labels required to allow the amplification product to be detected on the lateral flow device become incorporated or bound, for example, by hybridisation, to the product.

Once the amplification reaction is complete, the plunger (49) is operated, for example manually, although it may be arranged to be carried out automatically, if the device is disposed within a suitable apparatus. In some cases, it may be preferable to first draw up the plunger (49) so as to cause the contents of the well (41) including the amplification product, to be drawn back in the direction of the well (48) where it mixes with the diluent. The plunger (49) is then depressed. When this occurs, diluent (48) passes out of the reservoir (47) along the channel (46) and floods the well (41). As a result, the contents of the well (41) including the amplification reaction product are forced through the channel (44) into the second well (43). Liquid arriving in the well (43) encounters a first end region of wicking pad (50) and is absorbed into the pad (50). The other end region of the wicking pad (50) is in contact with a sample receiving portion of the membrane of the lateral flow device (45). The liquid therefore wicks along the pad (50) and is delivered to the lateral flow device in a reliable and controlled manner. As a result of the reagents present on the lateral flow device (45) and the inclusion of any binding or labelling reagents in the amplification reaction, a signal indicative of the presence or absence of target nucleic acid sample will develop on the lateral flow device (45).

Thus, this device provides a simple, easy to use and reliable means for carrying out an amplification and detection reaction, with minimum risk of contamination.

EXAMPLE 3

In the embodiment shown in FIG. 3, the first well (51) in which a nucleic acid amplification reaction can be carried out is provided within a housing (52) together with a second well (53) and a diluent well (54), linked together by channels (55,56) as in previous embodiments. In this case however, a further diluent well (57) is provided in addition to a first diluent well (52) which connects with the channel (56) by way of a channel (58). These channels (56,58) intersect at a "T" junction located upstream of the second well (53). As before, liquid contents of the second well (53) may be transferred to an LFD (59) by way of a pad of wicking fibre (60).

After a sample has been subject to a nucleic acid amplification reaction in the first well (51), the well (51) is flooded with diluent from well (54). Suitably, each of the diluent wells (54,57) are operated by means of a plunger (62, 63 respectively) and these are linked together by means of a lever (61) as illustrated in FIG. 4. Depression of the lever (61) in the direction shown by the arrow leads to the differential but controlled expulsion of diluent from both wells (52, 57) at different rates. The arrangement of the lever (61) is such as to provide mixing in the required proportions at the T junction. This will ensure that the contents from the first well are well mixed with diluent as they arrive in the second well (53).

Thereafter the mixture will pass along the pad of wicking fibre (60) and onto the sample receiving section of the LFD (59). A signal will thus develop in the LFD depending upon the presence or absence of amplified target nucleic acid.

EXAMPLE 4

A further embodiment of a device in accordance with the invention is shown in FIG. 5. In this figure, the device comprises a body (70). For ease of manufacture, the body (70) comprises upper and lower layers (70a and 70b respectively) between which is located a spacer (83) in which various structures as detailed below are defined. The body (70) is provided with a lateral projection (71) in which is accommodated a first reaction well (72) (FIG. 6) closable by means of a cap (73).

A channel (74) that is enclosed within the body (70) extends between the reaction well (72) and a second well (75), which is larger than the first well (72) and is embedded within the structure of the body (70). A wicking pad (76) projects into the second well (75). An end of the wicking pad (76) remote from the well (75) contacts a first end of an elongate bibulous membrane (77) of a lateral flow assay element. The membrane has thereon, either immobilised or free as is conventional in the art, binding agents and labelled binding agents that are specific for a particular target nucleic acid. These are arranged so that as liquid containing the target nucleic acid wicks along this by capillary flow from the wicking pad (76) to the remote end of the membrane (77), a visible signal will develop depending upon the presence or absence of the target within the liquid. Suitably the body (70) is transparent so that any signal may be seen. However, it would be possible to provide a viewing window within the body (70) to allow the development of signal to be seen if necessary.

The membrane (77) is arranged so that it traverses an aperture (78) within the body (70) and is supported along its length by a series of transverse struts (79), also embedded within the structure of the body (70).

A third well (80) for diluent is also provided within the body (70) and is closable by means of a plunger (81). The well (80) is also of greater volume than the reaction well (72) and is linked to the well (72) by means of a second channel (82).

In use, a chemical or biochemical reaction mixture such as a nucleic acid amplification reaction mixture is added to the well (72) and subject to appropriate conditions for example of temperature, to effect the required reaction therein. The projection (71) may be encased in a suitable heating apparatus to effect this. In this way, the conditions applied in the reaction well (72) are not applied to the remainder of the device where they may damage or deteriorate for example the membrane (77). Conditions applied will depend upon the particular reaction being effected which may comprise incubation at a relatively constant temperature for example in the case of isothermal nucleic acid amplification reactions, or thermal cycling between a range of temperatures such as is conventional reactions such as the polymerase chain reaction.

Thereafter, diluent is administered to the well (80) for example by being dispensed from a sealed container. If required, the sealed container may be preloaded within the well (80) which also contains a piercing means (not shown) and the diluent dispensed by pressing the container against the piercing means using the plunger (81).

Once dispensed, plunger (81) is depressed further forcing diluents along channel (82) into the well (72) where it mixes with the reaction mixture and overflows into the channel (74) and thereafter into the wicking pad (76). This will absorb the flowing liquid and pass it onto the first end region of the membrane (77). The liquid travels along the length of the membrane (77) by bibulous or capillary flow, during which process, it will become mixed with reagents such as labelling reagents and target elements such as target nucleic acids will develop a signal such as signal lines in the target and or control areas as is conventional in a lateral flow assay. These signals may be read through the body (70).

The device of FIGS. 5 and 6 may then be disposed of. Thus the invention provides a simple device that may be readily operated for a variety of purposes. It is simple to operate and minimises opportunities for contamination of samples and thus inaccurate results.

In a modified form of this device (FIG. 7), the projection (71) is solid but includes a downwardly projecting protrusion (83) that is able to form a snug fit with a detachable first well (72). Channels (74, and 82) pass through this protrusion 83 opening on the lower surface thereof. The separate first well (72) which is suitably preloaded with amplification reagents in dried form, is provided with an annular flange (84) for ease of handling. In this embodiment, there is no need for a separate cap (73). In use, a sample is applied to the first well (72) and the protrusion (83) is inserted snugly into the opening of the well (72) thus sealing it. Thereafter, the device may be used in the same way as described above in relation to the embodiment of FIG. 5.

EXAMPLE 5

The device substantially as illustrated in FIGS. 5 and 6 was used in a LAMP isothermal assay to detect the presence of a horse venereal disease in a sample. DNA from target bacteria lysed by boiling in water for 10 minutes was amplified using LAMP primers directed against the 16S ribosomal RNA gene of *Taylorella equigenitalis*. The loop primers of the reaction were labeled with either biotin or fluorescein and through these moieties the products associated with latex beads or the positive reaction areas on LFDs respectively. The amplification was conducted in the reaction well (72) (total volume 25 µl) using LAMP mastermix from GeneSys (Camberley, UK) being incubated at 65° C. for 20 minutes prior to dilution of the reaction, loaded on the device, in the appropriate buffer (225 µl of PBS). The buffer was loaded into well (80) and forced into the reaction well (72) by depressing plunger (81). The diluted amplification products were, concomitant with dilution, forced by positive pressure through the channel (74) and onto the LFD wicking material (76). The products of the reaction then travelled along the length of the LFD by capillary action with associated latex beads which accumulated (and thereby became visible) at the reaction area, both the test and control line. Lines were evident for the positive reaction at both the test (upper line) and control (lower line) indicating that the test material had been amplified and was positive.

The results, shown in FIG. 8, illustrate that the device and the method of the invention are effective and provide useful results.

The invention claimed is:

1. A self-contained device for carrying out an assay to detect a target nucleic acid in a sample, said device comprising:
   a central block;
   a first well in the central block, the first well configured to conduct a nucleic acid amplification reaction of a target nucleic acid;
   a lateral flow assay device in the central block;
   a first channel in the central block extending from said first well to the lateral flow assay device;
   a diluent well in the central block, the diluent well being connected to the first well by a second channel in the central block, and wherein the first well is of smaller volume than a volume of the diluent well;
   a sealed container of diluent received in the diluent well;
   a piercing means, wherein the piercing means is arranged such that the sealed container of diluent is punctured and opened to dispense the diluent into the diluent well when pressure is applied to the sealed container of diluent or the piercing means after completion of the nucleic acid amplification reaction;
   a cover plate engaged to the central block to close the first well, the first channel, the second channel, the lateral flow assay device, and the diluent well; and
   a sample well configured to receive a sample, the sample well connected to the first well, and wherein a sample well cover is configured to seal the sample well closed to close the device to additional fluids;
   wherein the lateral flow assay device is arranged to receive the sample from said first channel on a bibulous membrane thereof, and wherein said membrane contains elements that are configured to detect said target nucleic acid; and
   wherein, by applying pressure to the sealed container of diluent or the piercing means after completion of the nucleic acid amplification reaction, the diluent from the diluent well floods the first well by the second channel to force the sample from the first well to the lateral flow assay device.

2. The device according to claim 1 which further comprises a second well connected to said first well by the first channel, wherein the first channel is configured to transfer liquid contents of said first well to the second well and wherein the lateral flow assay device is configured to receive liquid contents from said second well on said bibulous membrane thereof.

3. The device according to claim 1 wherein the device comprises receiving means for the first well, and the first well is engageable with the receiving means.

4. The device according to claim 1 wherein the first well is separate from the device, and the first well attaches to the device.

5. The device according to claim 1 wherein the first well is preloaded with reagents suitable for carrying out the nucleic acid amplification reaction.

6. The device according to claim 2 wherein the first well is of smaller volume compared to the second well.

7. The device according to claim 2 wherein the first well, the second well, the channels, and the lateral flow assay device are contained within a housing.

8. The device according to claim 1 which further comprises a closed reagent well, the closed reagent well is preloaded with liquid reagents, and the closed reagent well is connected to the first well by another channel so that the contents of the closed reagent well are delivered into the first well.

9. The device according to claim 2 wherein a wicking element is provided between the second well and a sample receiving section of the lateral flow assay device, and the wicking element is configured to allow liquid from the second well to be delivered to said sample receiving section.

10. The device according to claim 1 which further comprises a nucleic acid extraction system, a nucleic acid purification system, or a nucleic acid extraction and purification system.

11. The device according to claim 1, and further comprising a reagent dispenser in the form of a plug, wand, or cap that is configured to fit into said first well, said reagent dispenser including at least some of the reagents required to carry out the nucleic acid amplification reaction.

12. The device according to claim 1, and further comprising a heater arranged to controllably heat said first well so as to allow the nucleic acid amplification reaction to be carried out therein.

13. The device according to claim 12, wherein the device comprises an additional well in which cell lysis takes place, and wherein the device includes a heater for heating said additional well to effect lysis.

14. A self-contained device for carrying out a chemical or biochemical reaction and detecting a product thereof, said device comprising:
   a central block;
   a first well in the central block, the first well configured to conduct the chemical or biochemical reaction in a liquid phase;
   a lateral flow assay device in the central block;
   a first channel in the central block extending from said first well to a second well and to the lateral flow assay device;
   wherein the lateral flow assay device is configured to receive liquid contents from said first channel, by way of the second well, on a bibulous membrane thereof, wherein said membrane contains elements configured to detect a product of said chemical or biochemical reaction;
   a sealed container of diluent, wherein a third well receives the sealed container of diluent within the third well;
   a piercing means, wherein the piercing means is arranged such that the sealed container of diluent is punctured and opened to dispense the diluent into the third well when pressure is applied to the sealed container of diluent or the piercing means after completion of the chemical or biochemical reaction;
   wherein the third well is connected to said first well, by a second channel, wherein the second channel is configured such that the diluent from said third well is transferred to the first well, and wherein the volume of the second and third wells is greater than that of the first well;

a cover plate engaged to the central block to close the first well, the first channel, the second channel, the lateral flow assay device, and the third well; and a fourth well configured to receive a sample, the fourth well connected to the first well, wherein a fourth well cover is configured to seal the fourth well closed to close the device to additional fluids, and wherein, by applying pressure to the sealed container of diluent or the piercing means after completion of the chemical or biochemical reaction, the diluent from the third well floods the first well to force the sample from the first well to the lateral flow assay device.

15. A method for carrying out a chemical or biochemical reaction and detecting the product thereof on a membrane of a lateral flow assay device, said method comprising adding the sample to the first well of the device according to claim 14, subjecting said first well to conditions under which said chemical or biochemical reaction occurs, thereafter transferring the diluent present in said third well of the device to said first well by applying pressure to the sealed container of diluent or the piercing means after completion of the chemical or biochemical reaction so as to cause the contents to flow along the first channel to the said second well and thereafter along the membrane of the lateral flow assay device, and thereafter reading the results therefrom.

16. The device according to claim 1 wherein the volume of the first well is 15-50 µl and the volume of the diluent well is 50-250 µl.

17. A self-contained device for carrying out an assay to detect a target nucleic acid in a sample, said device comprising:

a housing comprising a central block, an upper cover plate, and a lower base plate;

a first well in the central block, the first well configured to conduct a nucleic acid amplification reaction of a target nucleic acid;

a lateral flow assay device in the central block;

a first channel in the central block extending from said first well to the lateral flow assay device;

a diluent well in the central block, the diluent well being connected to the first well by a second channel in the central block, and wherein the first well is of smaller volume than a volume of the diluent well;

a sealed container of diluent received in the diluent well;

a piercing means, wherein the piercing means is arranged such that the sealed container of diluent is punctured and opened to dispense the diluent into the diluent well when pressure is applied to the sealed container of diluent or the piercing means after completion of the nucleic acid amplification reaction; and a sample well configured to receive a sample, the sample well connected to the first well, and wherein a sample well cover is configured to seal the sample well closed to close the device to additional fluids;

wherein the first well, the sample well, the first channel, the second channel, the lateral flow assay device and the diluent well are in the central block, and the central block is covered by the upper cover plate, and the lower base plate is beneath the central block;

wherein the lateral flow assay device is arranged to receive an amplification product from the sample from said first channel on a bibulous membrane thereof, and wherein said membrane contains elements configured to detect target nucleic acid; and wherein, by applying pressure to the sealed container of diluent or the piercing means after completion of the nucleic acid amplification reaction, an overflow of the diluent from the diluent well flows to the first well by the second channel and drives the amplification product from the first well to the lateral flow assay device.

18. A self-contained device for carrying out an assay to detect a target nucleic acid in a sample, said device comprising:

a housing comprising a central block, an upper cover plate, and a lower base plate;

a first well in the central block, the first well configured for conducting a nucleic acid amplification reaction of a target nucleic acid;

a lateral flow assay device in the central block;

a first channel in the central block extending from said first well to the lateral flow assay device;

a diluent well in the central block, the diluent well being connected to the first well by a second channel in the central block, and wherein the first well is of smaller volume than a volume of the diluent well;

a sealed container of diluent received in the diluent well;

a piercing means, wherein the piercing means is arranged such that the sealed container of diluent is punctured and opened to dispense the diluent into the diluent well when pressure is applied to the sealed container of diluent or the piercing means after completion of the nucleic acid amplification reaction;

wherein the cover plate is engaged to the central block to close the first well, the first channel, the second channel, the lateral flow assay device, and the diluent well;

a sample well configured to receive a sample, the sample well connected to the first well, and wherein a sample well cover is configured to seal the sample well closed to close the device to additional fluids;

wherein the first well, the sample well, the first channel, the second channel, the lateral flow assay device and the diluent well are in the central block, and the central block is covered by the upper cover plate, and the lower base plate is beneath the central block;

wherein the lateral flow assay device is configured to receive the sample from said first channel on a bibulous membrane thereof, and wherein said membrane contains elements that are configured to detect said target nucleic acid; and wherein the diluent from the sealed container within the device is transferred to the diluent well by applying pressure to the sealed container of diluent or the piercing means after completion of the nucleic acid amplification reaction, and the diluent from the diluent well floods the first well by the second channel to force the sample from the first well to the lateral flow assay device.

* * * * *